US008070674B1

(12) United States Patent
Hughes

(10) Patent No.: US 8,070,674 B1
(45) Date of Patent: Dec. 6, 2011

(54) SEX ENHANCER

(76) Inventor: P. Jane Hughes, Mason City, IL (US)

( * ) Notice: Subject to any disclaimer, the term of this patent is extended or adjusted under 35 U.S.C. 154(b) by 1414 days.

(21) Appl. No.: 11/340,074

(22) Filed: Jan. 25, 2006

Related U.S. Application Data

(60) Provisional application No. 60/647,570, filed on Jan. 27, 2005.

(51) Int. Cl.
*A61F 5/00* (2006.01)

(52) U.S. Cl. .......................................................... 600/38

(58) Field of Classification Search .............. 600/38–41; 623/7–8
See application file for complete search history.

(56) References Cited

U.S. PATENT DOCUMENTS

| | | | | |
|---|---|---|---|---|
| 4,066,075 | A | 1/1978 | Hughes | 128/127 |
| 4,922,928 | A | 5/1990 | Burnhill | 128/832 |
| 4,944,750 | A * | 7/1990 | Cox, Jr. | 623/8 |
| 5,133,753 | A * | 7/1992 | Bark et al. | 623/8 |
| 5,993,377 | A * | 11/1999 | Hartwig | 600/38 |
| 6,170,484 | B1 | 1/2001 | Feng | 128/830 |
| 6,328,991 | B1 | 12/2001 | Myhling | 424/430 |
| 6,723,031 | B1 * | 4/2004 | Wild | 600/38 |
| 2002/0038658 | A1 | 4/2002 | Austin et al. | 128/830 |

* cited by examiner

*Primary Examiner* — John Lacyk
(74) *Attorney, Agent, or Firm* — Philip L. Bateman

(57) ABSTRACT

A sex enhancer is a flexible and deformable fluid-filled enclosure with a smooth exterior surface having a rounded shape. The sex enhancer is heated and inserted into the vagina before sexual intercourse. During sexual intercourse, the penis pushes the sex enhancer against the cervix to provide enhanced pleasure to the woman without detracting from the pleasure of the man.

5 Claims, 2 Drawing Sheets

SEX ENHANCER

CROSS-REFERENCE TO RELATED APPLICATION

This application claims the benefit of U.S. Provisional Application Ser. No. 60/647,570, Jan. 27, 2005.

FIELD OF THE INVENTION

This invention relates to sexual appliances. More particularly, this invention relates to an intravaginal sex enhancer.

BACKGROUND OF THE INVENTION

Humans reproduce by sexual intercourse in which a man inserts his penis inside a woman's vagina. When the man ejaculates, sperm flow out of the penis, into the vagina, up through the opening in the cervix, and into the uterus. Conception occurs if one of the sperm fertilizes an egg passing through the uterus.

Humans engage in sex for reasons other than reproduction. Sex is very pleasurable physically and emotionally for both men and women. Men experience an orgasm at ejaculation and women can also experience orgasm during sex. It is still a subject of debate whether the evolutionary purpose of the female orgasm is to draw the sperm into the uterus or is simply to provide pleasure. During sexual intercourse, women receive physical pleasure from the stimulation of the clitoris and nerve endings in the vagina by the motion of the penis.

Women also receive pleasure when the head of the penis contacts the cervix. Unfortunately, the vast majority of men's penises are not long enough to reach the cervix. A variety of penis extenders have been disclosed for men desiring longer and/or thicker penises. The extenders are typically made of latex and fit over the head of the penis. They detract from the man's pleasure because they eliminate the contact between the head of the penis and the inner wall of the vagina. Unlike the spongy head of an erect penis, these extenders are hard with little ability to deform. And unlike a penis, these extenders are typically colder than body temperature. For these reasons, most women feel the penis extenders provide little pleasure and some women feel they actually detract from the pleasure.

A variety of intravaginal devices have been disclosed that, if present during sexual intercourse, could be pushed against the cervix by the penis. However, these devices are cold, hard, and/or of the wrong shape or size to provide pleasure. Examples of such devices include the contraceptive devices disclosed in Hughes, U.S. Pat. No. 4,066,075, issued Jan. 3, 1978; Burnhill, U.S. Pat. No. 4,922,928, issued May 8, 1990; Feng, U.S. Pat. No. 6,170,484, issued Jan. 9, 2001; Myhling, U.S. Pat. No. 6,328,991, issued Dec. 11, 2001; and Austin et al., U.S. Pat. Appln. Publn. No. US2002/0038658, published Apr. 4, 2002

Accordingly, there is a demand for a sex enhancer that provides pleasurable contact with the cervix during sexual intercourse in the same manner as an exceptionally long penis without detracting from the pleasure of the man.

SUMMARY OF THE INVENTION

One general object of this invention is to provide an improved sex enhancer. A more particular object is to provide a sex enhancer that provides pleasurable contact with the cervix during sexual intercourse in the same manner as an exceptionally long penis without detracting from the pleasure of the man. Another general object of this invention is to provide a method of enhancing pleasure to the woman during sexual intercourse without detracting from the pleasure of the man.

I have invented an improved sex enhancer. The sex enhancer comprises a flexible and deformable fluid-filled enclosure with a smooth exterior surface having a rounded shape. The sex enhancer is adapted for heating and insertion into the vagina before sexual intercourse such that the penis pushes the sex enhancer against the cervix to provide enhanced pleasure to the woman without detracting from the pleasure of the man.

I have also invented a method of enhancing pleasure to the woman during sexual intercourse without detracting from the pleasure of the man. The method comprises inserting a flexible and deformable fluid-filled enclosure with a smooth exterior surface having a rounded shape into the vagina before sexual intercourse such that the penis pushes the sex enhancer against the cervix.

The sex enhancer of this invention is safe, easy to use, and very effective at enhancing pleasure to the woman during sexual intercourse without detracting from the pleasure of the man. Similarly, the method of this invention enhances pleasure to the woman during sexual intercourse without detracting from the pleasure of the man.

DETAILED DESCRIPTION OF THE INVENTION

This invention is best understood by reference to the drawings. The sex enhancer 10 is a fluid-filled enclosure that is inserted into the vagina before sexual intercourse. It is pushed against the cervix by the penis during intercourse, thus providing enhanced pleasure to the woman without detracting from the pleasure of the man.

The enclosure is flexible, pliable, and deformable. It is preferably made of an elastomeric material in sheet or fabric form. Suitable elastomers include natural latex rubber and synthetic elastomers such as polyurethanes, polyolefins (such as polyester), silicons, butadiene copolymers, or the like. The enclosure is non-permeable so that the fluid does not escape through the material. The enclosure wall is preferably thick enough so that rupturing or leaking is unlikely. The enclosure wall is generally about 0.01 to 0.3 inches thick and preferably about 0.05 to 0.2 inches thick. Reusable models generally have slightly thicker walls than disposable models. The enclosure is preferably resistant to the fluids, lubricants, etc. that are sometimes present during sexual intercourse.

The enclosure has a smooth exterior surface. The term "smooth" means there are no projections, jagged edges, or fittings that would cause discomfort to the man or woman. An exterior surface containing small ridges or the like such as those in textured condoms is included within the smooth definition.

Figure 2:
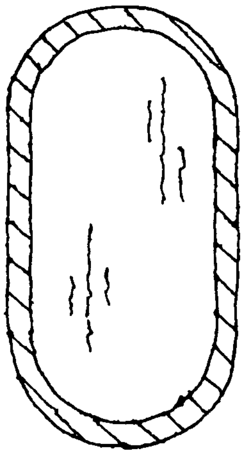
FIG. 2 is a sectional side view thereof.
Figure 3:
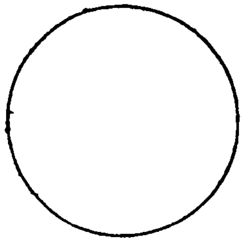
FIG. 3 is an end view thereof.
Figure 1:
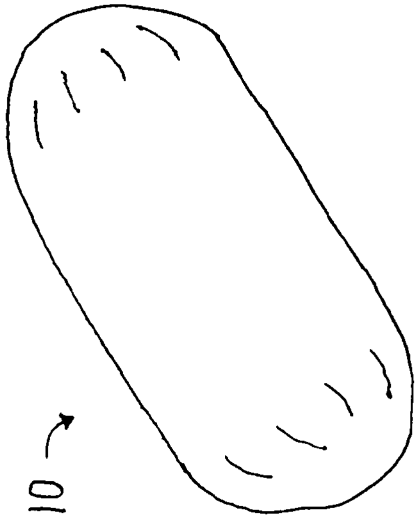
FIG. 1 is a perspective view of a preferred embodiment of the sex enhancer of this invention.

The enclosure has a rounded shape to conform to the shape of the vaginal canal. A sphere is suitable if the man's penis is long and reaches within one or two inches of the cervix at full penetration. The diameter of the sphere is limited by the width of the vagina and, therefore, a sphere may not add sufficient length to reach the cervix for many couples. Therefore, a slightly elongated shape that corresponds to the shape of the vaginal canal is preferred in most cases. As best seen in FIG. 2, the enclosure of the preferred embodiment has the shape of a cylinder with domes on the ends, like that of a hot dog except of different proportions. Alternatively, the enclosure can be egg shaped or can have the shape of an elongated spheroid (also known as a prolate spheroid) in which the sides bulge outward.

The enclosure has a size that is small enough to easily fit into the vagina and yet large enough to provide a pleasurable sensation. In general, the thickness of the enclosure is about three-fourths to three inches and the length is about one to six inches. The enclosure preferably has a thickness of about one to two inches and a length of about two to three inches. This thickness is comparable to the thickness of most penises and this length is sufficient for most penises to push the enclosure against the cervix when full penetration occurs.

The enclosure is filled with a fluid. The fluid is non-toxic so that a rupture or leak causes no problems to the user. The fluid preferably has a relatively high heat capacity so it retains its temperature during use. Suitable fluids include water, with or without dissolved materials such as salts, sugars, or the like for density adjustment. Other suitable fluids include silicones, oils, gels, and the like. The fluid preferably comprises water. In other words, the preferred fluids are pure water and water solutions such as saline (water with dissolved sodium chloride).

A large amount of art exists on the construction of breast implants. Most breast implants are made with the type of material and fluid that are suitable for the enclosure of this invention. The enclosure is, however, of a different shape.

Figure 4:
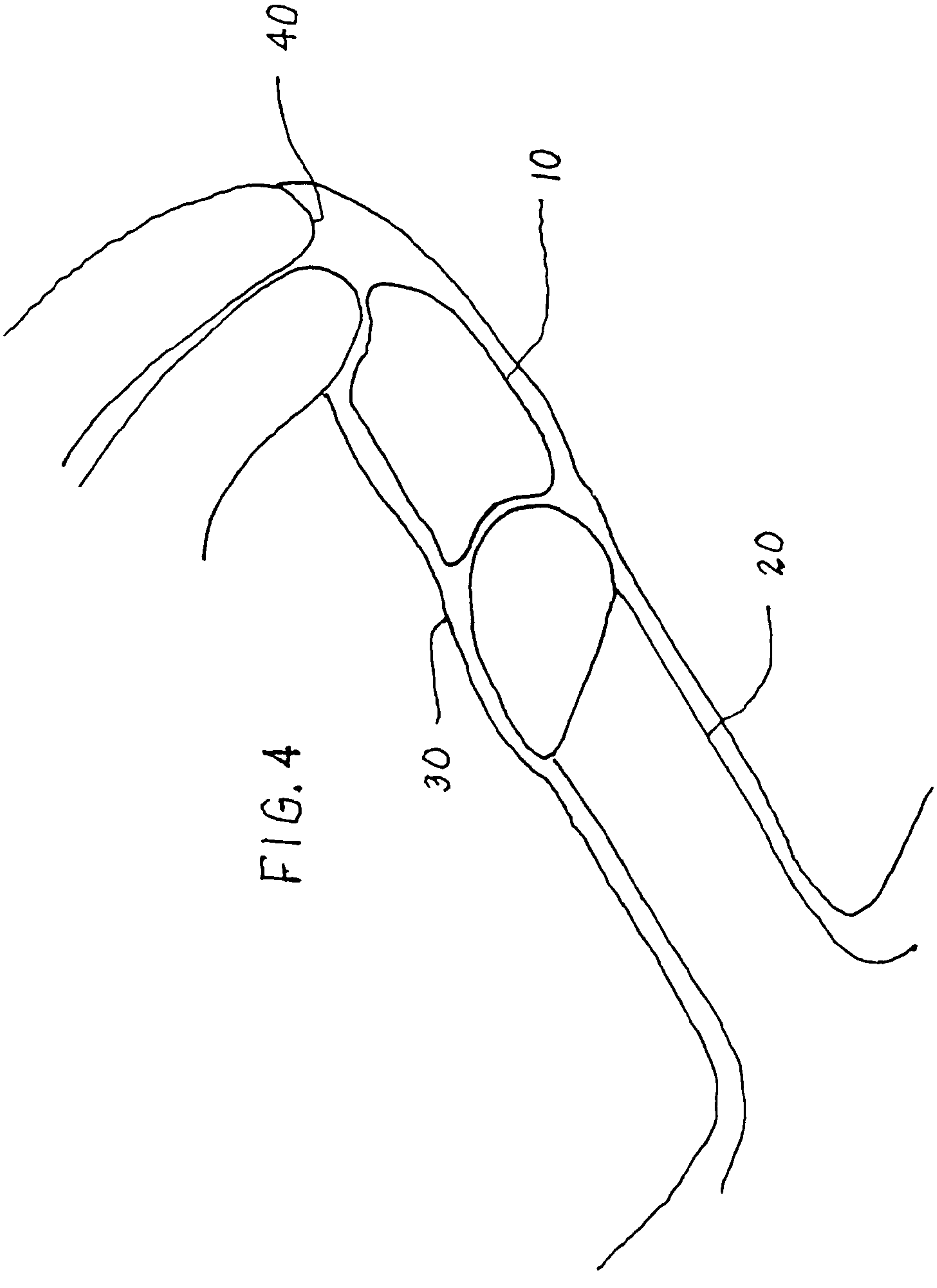
FIG. 4 is a representation of its use during sexual intercourse.

The use of the sex enhancer is illustrated in FIG. 4. Before sexual intercourse, the sex enhancer is typically heated to about body temperature. The sex enhancer is then inserted into the vagina. Although body temperature is preferred by most couples, some couples enjoy having the sex enhancer at a different temperature, either below or above body temperature. The heating or cooling can take place in a variety of ways. For example, the sex enhancer can be placed into a microwave oven if the fluid is water or it can be submerged in water of the desired temperature in a sink or bowl.

During sexual intercourse, the penis 20 within the vagina 30 pushes the sex enhancer against the cervix 40. The sex enhancer deforms around the penis in such a way that it is difficult for the man to tell that the sex enhancer is in place if the sex enhancer is at body temperature. On the other hand, the woman notices a significant enhancement in pleasure when the sex enhancer is forced against her cervix. The sex enhancer deforms at the cervix so the pressure against the cervix is gentle.

After sexual intercourse, the sex enhancer is easily expelled by muscular action. The sex enhancer can be easily cleaned with conventional cleaners and it takes up little storage space. Alternatively, the sex enhancer can be disposed after each use.

The sex enhancer provides enhanced pleasure to the woman without detracting from the physical pleasure of the man. Some men find that the sex enhancer also enhances their physical pleasure. However, regardless of whether a man's physical pleasure is enhanced or simply not reduced, all men find that the overall sexual experience is enhanced when their partners receive more pleasure. Therefore, the sex enhancer is as popular with men as it is with women.

I claim:

1. A method of enhancing pleasure to the woman during sexual intercourse without detracting from the pleasure of the man, the method comprising inserting a sex enhancer device comprising a flexible and deformable enclosure with a completely smooth exterior surface having a rounded shape, being completely filled with a fluid and being unconnected to another enclosure and having no means for connection to another enclosure, into the vagina before sexual intercourse and then having sexual intercourse such that the penis pushes the sex enhancer device against the cervix.

2. The method of claim 1 wherein the fluid in the enclosure of the sex enhancer device comprises water.

3. The method of claim 2 wherein the enclosure of the sex enhancer device is an elongated spheroid having a thickness of about one to three inches and a length of about three-fourths to six inches.

4. The method of claim 3 wherein the enclosure of the sex enhancer device is made of a material comprising a synthetic elastomer having a thickness of about 0.01 to 0.3 inches.

5. The method of claim 4 wherein the sex enhancer device is heated to about body temperature before insertion.

* * * * *